(12) United States Patent
Laitinen et al.

(10) Patent No.: US 7,767,813 B2
(45) Date of Patent: Aug. 3, 2010

(54) PREPARATION METHOD

(75) Inventors: Ilpo Laitinen, Espoo (FI); Hannele Nikander, Espoo (FI)

(73) Assignee: Fermion Oy, Espoo (FI)

( * ) Notice: Subject to any disclaimer, the term of this patent is extended or adjusted under 35 U.S.C. 154(b) by 43 days.

(21) Appl. No.: 11/883,581

(22) PCT Filed: Feb. 6, 2006

(86) PCT No.: PCT/FI2006/000033

§ 371 (c)(1), (2), (4) Date: Sep. 24, 2007

(87) PCT Pub. No.: WO2006/084941

PCT Pub. Date: Aug. 17, 2006

(65) Prior Publication Data

US 2008/0161572 A1   Jul. 3, 2008

Related U.S. Application Data

(60) Provisional application No. 60/650,523, filed on Feb. 8, 2005.

(51) Int. Cl.
C07D 519/00 (2006.01)

(52) U.S. Cl. ............................................... 546/48

(58) Field of Classification Search .............. 546/48
See application file for complete search history.

(56) References Cited

U.S. PATENT DOCUMENTS

| | | | |
|---|---|---|---|
| 4,473,692 A | 9/1984 | Miyasaka et al. | |
| 4,604,463 A | 8/1986 | Miyasaka et al. | |
| 4,894,456 A | 1/1990 | Wall et al. | |
| 5,053,512 A | 10/1991 | Wani et al. | |
| 6,121,451 A * | 9/2000 | Henegar et al. | 546/92 |
| 6,444,820 B1 * | 9/2002 | Henegar et al. | 546/48 |
| 6,476,043 B1 * | 11/2002 | Toutain et al. | 514/280 |
| 6,723,729 B2 | 4/2004 | Henegar | |
| 2004/0106830 A1 | 6/2004 | Ogawa et al. | |
| 2008/0103309 A1 * | 5/2008 | Laitinen | 546/48 |
| 2008/0182990 A1 * | 7/2008 | Vishnukant et al. | 546/48 |

FOREIGN PATENT DOCUMENTS

| | | |
|---|---|---|
| EP | 1 378 505 A1 | 1/2004 |
| WO | WO-96/31513 A1 | 10/1996 |
| WO | 02/066416 * | 8/2002 |
| WO | WO 03/074527 A | 9/2003 |
| WO | 03/089413 * | 10/2003 |
| WO | WO-2005/117879 A1 | 12/2005 |

OTHER PUBLICATIONS

Shutske et al., "A novel synthesis of the isoxazolo[5,4-kl]acriding ring system," J. Heterocyclic Chem., vol. 27, No. 6, 1990, pp. 1617-1621, XP002386600.
Third Party Observations under Article 115 EPC—EP Application No. 06 708 891.4 (EP 1 846 371) (May 16, 2009).
Third Party Observations Pursuant to Article 115 EPC—EP Application. No. 06 708 891.4 (EP 1 846 371) (Apr. 17, 2009).
Sawada S et al., Pharmaceutical Society of Japan, vol. 39, No. 6, Jun. 1, 1991, pp. 1446-1454.
Henegar K E et al., Journal of Organic Chemistry, American Chemical Society, vol. 62, No. 19, 1997, pp. 6588-6597.

* cited by examiner

*Primary Examiner*—D. Margaret Seaman
*Assistant Examiner*—Niloofar Rahmani
(74) *Attorney, Agent, or Firm*—Birch, Stewart, Kolasch & Birch, LLP

(57) ABSTRACT

The present invention is directed to a novel method for the preparation of high purity irinotecan. This can be achieved by eliminating the excess of the other reagent, bipiperidinyl-1'-carbonyl chloride after it has reacted with 7-ethyl-10-hydroxy camptothecin and crystallizing the final product from a suitable solvent.

5 Claims, No Drawings

PREPARATION METHOD

This application is the National Phase of PCT/FI2006/000033 filed on Feb. 6, 2006, which claims priority under 35 U.S.C. §119(e) on U.S. Provisional Application No(s). 60/650,523 filed on Feb. 8, 2005, the entire contents of which are hereby incorporated by reference.

FIELD OF THE INVENTION

The invention relates to a process for the preparation of (S)-4,11-diethyl-3,4,12,14-tetrahydro-4-hydroxy-3,14-dioxo-1H-pyrano[3',4':6,7]-indolizino[1,2-b]quinolin-9-yl[1,4'-bipiperidine]-1'-carboxylate or a pharmaceutically acceptable salt thereof.

BACKGROUND OF THE INVENTION

Irinotecan hydrochloride, (S)-4,11-diethyl-3,4,12,14-tetrahydro-4-hydroxy-3,14-dioxo-1H-pyrano[3',4':6,7]-indolizino[1,2-b]quinolin-9-yl[1,4'-bipiperidine]-1'-carboxylate hydrochloride or 7-ethyl-10-[4-(1-piperidino)-1-piperidino]carbonyloxycamptothecin hydrochloride (CPT-11), having the formula I

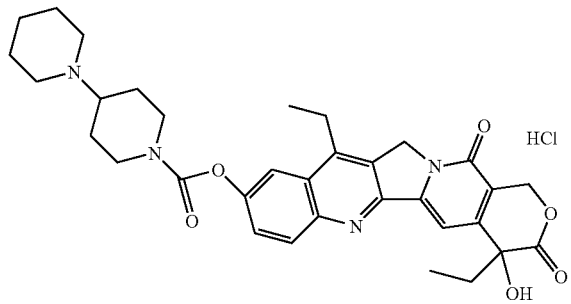

is a camptothecin analog and topoisomerase I inhibitor. Its trihydrate form has been approved in 1996 in the United States for the treatment of colon cancer, but it is also of interest for treatment of other cancers, such as cancers of the lung, the stomach and the pancreas.

Irinotecan is usually prepared semisynthetically from natural camptothecin, which is extracted from a Chinese tree, *Camptotheca acuminata*. U.S. Pat. No. 4,604,463 describes several camptothecin derivatives, including irinotecan, its pharmaceutically acceptable salts and preparation thereof starting from natural camptothecin. U.S. Pat. No. 6,121,451 discloses intermediates and process for the synthesis of camptothecin derivatives, e.g. irinotecan hydrochloride, including synthetic route to starting material, 7-ethyl-10-hydroxy camptothecin.

Sawada et al., Chem. Pharm. Bull. 39(6), 1446-1454 (1991), describes the preparation of irinotecan hydrochloride trihydrate from natural camptothecin in five steps and about 20% of overall yield. Similar process is described also in U.S. Pat. No. 6,723,729. WO 03/074527 describes a new anhydrous polymorphic form of irinotecan hydrochloride, and its preparation. This polymorphic form is said to have improved solubility properties compared to the known trihydrate.

Now we have surprisingly found out that irinotecan can be produced in high yield and purity from 7-ethyl-10-hydroxy camptothecin and [1,4']-bipiperidinyl-1'-carbonyl chloride or its hydrochloride, if the excess of [1,4']-bipiperidinyl-1'-carbonyl chloride is eliminated after the reaction and the product is isolated by crystallization.

DETAILED DESCRIPTION OF THE INVENTION

The present invention is directed to a novel method for the preparation of high purity irinotecan. This can be achieved by eliminating the excess of the other reagent, [1,4']-bipiperidinyl-1'-carbonyl chloride, which may be used as a hydrochloride, after it has reacted with 7-ethyl-10-hydroxy camptothecin, and crystallizing the final product from a suitable solvent. The elimination of the excess of [1,4']-bipiperidinyl-1'-carbonyl chloride can be made by adding a suitable amine.

Natural camptothecin, as well as irinotecan available commercially, is known to have the S-configuration at the 20-position. Synthetic derivatives can be made as racemic compounds or as enantiomerically pure substances, which, as well as pharmaceutically acceptable salts thereof, are included in the invention. Resolution can be made after the synthesis, during the synthesis, or desired enantiomers can be used as starting compounds.

A process for the preparation of irinotecan hydrochloride trihydrate comprises the steps of: a) reacting 7-ethyl-10-hydroxy camptothecin with [1,4']-bipiperidinyl-1'-carbonyl chloride, b) eliminating excess [1,4']-bipiperidinyl-1'-carbonyl chloride after the reaction, c) adding hydrochloric acid to make irinotecan hydrochloride, d) crystallizing irinotecan hydrochloride, e) isolating crystalline irinotecan hydrochloride, and f) transforming the irinotecan hydrochloride to irinotecan hydrochloride trihydrate by crystallizing from a suitable solvent.

The other starting material, 7-ethyl-10-hydroxycamptothecin may be natural or preferably, made synthetically e.g. as described in U.S. Pat. No. 6,121,451 which is incorporated herein by reference. [1,4']-bipiperidinyl-1'-carbonyl chloride or its hydrochloride may be made e.g. as described in EP 976733.

The reaction is performed in a suitable solvent system comprising pyridine and another solvent to dissolve [1,4']-bipiperidinyl-1'-carbonyl chloride. This another solvent may be e.g. chlorinated hydrocarbon, e.g. methylene chloride may be used. If [1,4']-bipiperidinyl-1'-carbonyl chloride hydrochloride is used, it is first liberated to a base using a suitable amine base, e.g. triethylamine.

Excess of [1,4']-bipiperidinyl-1'-carbonyl chloride is eliminated by adding a suitable reagent, with which it reacts to form easily removable reaction products. They are e.g. compounds which remain in the mother liquor from which irinotecan hydrochloride will be crystallized. Primary or secondary amines can be used as reagents, and preferably 4-piperidinopiperidine is used. The removal of the excess of [1,4']-bipiperidinyl-1'-carbonyl chloride diminishes the formation of additional side products, which are difficult to remove in later phases. The reagent is used 0.1 to 0.5 molar equivalents to 7-ethyl-10-hydroxy camptothecin, preferably 0.25 to 0.35 equivalents.

Crude irinotecan hydrochloride is crystallized from a suitable crystallization solvent which may be selected from alcohols, nitriles, and their mixtures with water. E.g. acetonitrile, ethanol or butanol, or their mixtures with water can be used. Before the addition of the crystallization solvent most of the reaction solvent is distilled off. The resulting crystalline product has a purity as measured by High Performance Liquid Chromatography (HPLC, area % of the main peak) of at least 99.8%, even 99.9%, without any additional purification steps like chromatographic purification which have been used in prior art processes.

In earlier publications irinotecan hydrochloride trihydrate is made from irinotecan base and hydrochloric acid by crystallizing from water or from its mixture with acetonitrile. The product has been dried in vacuo and thereafter kept in a humidity chamber to obtain trihydrate.

Irinotecan hydrochloride made according to the present invention can be crystallized as trihydrate from water or from its mixture with ethanol. Adding ethanol to the crystallization solvent improves the dissolution profile and lower temperatures can be used. Alcohol may be used in the crystallization solvent up to about 40% (v/v), e.g. water:alcohol ratio from 3:1 to 2:1 may be used.

Irinotecan hydrochloride is dissolved in the selected solvent or mixture of solvents and heated to nearly boiling and filtered. The filtered solution is cooled preferably in a controlled way to a suitable temperature where seed crystals are optionally added. Adding of seed crystals may take place in about 65° C. Thereafter cooling is continued until the temperature about 20° C. is achieved; even lower temperatures may be used. Crystal size distribution can be controlled by controlling the cooling rate. Larger crystals are obtained if the cooling from 65° C. to about 50° C. is carried out slowly in about 5 to 20 hours and from that to about 20° C. also in about 5 to 20 hours. Total cooling time may be about 10 to 40 hours, e.g. total cooling time from 15 to 20 hours can be used. If the cooling from boiling to ambient temperature is carried out fast, in about 2 to 3 hours, the crystals formed are very small, even smaller than 20 μm, but using the cooling profile described, larger crystals, which are easy to filter, with medium length of about 50 μm to 200 μm, are obtained. The trihydrate crystals formed are isolated and washed, and they are dried to remove excess water. Depending on the purity of the starting materials, the HPLC purity of the final product is even 99.9% or higher.

EXAMPLES

Example 1

(S)-4,11-diethyl-3,4,12,14-tetrahydro-4-hydroxy-3, 14-dioxo-1H-pyrano[3',4':6,7]-indolizino[1,2-b] quinolin-9-yl[1,4'-bipiperidine]-1'-carboxylate hydrochloride 7-Ethyl-10-hydroxycamptothecin (4.5 g) and pyridine (60 ml) were charged in a reaction vessel. A solution of [1,4']-bipiperidinyl-1'-carbonyl chloride hydrochloride (3.44 g) and triethylamine (4.8 ml) in 75 ml of methylene chloride was added at 30-40° C. The mixture was stirred for 1.5 hours at 30-40° C. 4-piperidinopiperidine (0.58 g) was added and the mixture was stirred for 0.5 hour. Methylene chloride and pyridine were distilled off until the volume of the residue was about 25 ml. Acetonitrile (100 ml) was added and the mixture was heated to about 60° C. The mixture was cooled to room temperature and 15 ml of 5% aqueous hydrochloric acid was added. The mixture was stirred about 20 hours at room temperature. The mixture was cooled to 0±5. The crystalline compound was filtered and washed with acetonitrile:water 10:1 mixture (10 ml) and acetonitrile (10 ml). The product was dried under reduced pressure. The yield was 6.4 g (90%).

Example 2

(S)-4,11-diethyl-3,4,12,14-tetrahydro-4-hydroxy-3, 14-dioxo-1H-pyrano[3',4':6,7]-indolizino[1,2-b] quinolin-9-yl[1,4'-bipiperidine]-1'-carboxylate hydrochloride trihydrate (S)-4,11-diethyl-3,4,12,14-tetrahydro-4-hydroxy-3,14-dioxo-1H-pyrano[3',4':6,7]-indolizino[1,2-b]quinolin-9-yl[1, 4'-bipiperidine]-1'-carboxylate hydrochloride (6.83 g), 36 ml of water and 18 ml of ethanol were charged in a reaction vessel. The mixture was heated to reflux and the solution was filtered at about 70° C. The solution was cooled to room temperature in about three hours adding seed crystals at 65° C. The mixture was stirred for about 20 hours at room temperature and cooled to 0±5° C. The crystalline product was filtered and washed with water (10 ml).

The product was dried under reduced pressure at room temperature until the water content was 8.0% ($3H_2O$).

The yield was 6.37 g (82% from 7-ethyl-10-hydroxy camptothecin).

The HPLC-purity was 99.9%. The average particle length was <20 μm by microscopic analysis.

Example 3

(S)-4,11-diethyl-3,4,12,14-tetrahydro-4-hydroxy-3, 14-dioxo-1H-pyrano[3',4':6,7]-indolizino[1,2-b] quinolin-9-yl[1,4'-bipiperidine]-1'-carboxylate hydrochloride trihydrate Irinotecan HCl (4.8 g), water (30 ml), ethanol (10 ml) and 5% HCl (0.3 ml) were charged. The mixture was heated to 75-80° C. and stirred until all dissolved. The solution was cooled to 65° C. and seed crystals were added. The solution was cooled in 10 hours to 50° C. and in 10 hours to 20° C. The crystalline compound was filtered and washed with water (16 ml).

The product was dried under normal pressure at room temperature.

The yield of irinotecan HCl $3H_2O$ was 4.6 g (87%).

The HPLC-purity was 99.9%. Based on X-ray and IR analysis the product is form b as defined in WO 03/074527.

The average length of the crystals was 50 μm-200 μm by microscopic analysis.

The invention claimed is:

1. A process for the preparation of irinotecan hydrochloride comprising:
   a) reacting 7-ethyl-l10-hydroxy camptothecin with [1,4']-bipiperidiny-1'-carbonyl chloride;
   b) eliminating the excess of [1,4']-bipiperidiny11'-carbonyl chloride after the reaction by adding primary or secondary amine;
   c) adding hydrochloric acid to make irinotecan hydrochloride; and
   d) crystallizing irinotecan hydrochloride.

2. A process for the preparation of irinotecan hydrochloride trihydrate comprising:
   a) reacting 7-ethyl-10 -hydroxy camptothecin with [1,4']-bipiperidiny11 '-carbonyl chloride;
   b) eliminating the excess of [1,4]-bipiperidiny-1'-carbonyl chloride after the reaction by adding primary or secondary amine;
   c) adding hydrochloric acid to make irinotecan hydrochloride;
   d) crystallizing irinotecan hydrochloride;
   e) isolating crystalline irinotecan hydrochloride; and f) transforming the irinotecan hydrochloride to irinotecan hydrochloride trihydrate by crystallizing from a suitable solvent.

3. The process of claim 1 or 2, wherein said amine is 4-piperidinopiperidine.

4. The process of claim 2 wherein the solvent in step f) is water.

5. The process of claim 2 for the preparation of irinotecan hydrochloride trihydrate which has purity as measured by High Performance Liquid Chromatography (HPLC) of at least 99.9%.

* * * * *